US007613495B2

(12) United States Patent
Hutchinson (10) Patent No.: US 7,613,495 B2
(45) Date of Patent: Nov. 3, 2009

(54) MRI DETECTION AND STAGING OF PARKINSON'S DISEASE AND DETECTION OF PROGRESSIVE SUPRANUCLEAR PALSY

(75) Inventor: Michael Hutchinson, New York, NY (US)

(73) Assignee: Advanced MRI Technologies, LLC, Sebastopol, CA (US)

( * ) Notice: Subject to any disclaimer, the term of this patent is extended or adjusted under 35 U.S.C. 154(b) by 109 days.

(21) Appl. No.: 09/997,894

(22) Filed: Nov. 30, 2001

(65) Prior Publication Data

US 2002/0115930 A1  Aug. 22, 2002

Related U.S. Application Data

(60) Provisional application No. 60/250,301, filed on Nov. 30, 2000.

(51) Int. Cl.
*A61B 5/055* (2006.01)
(52) U.S. Cl. ...................................... 600/410
(58) Field of Classification Search ............. 600/420, 600/407, 410; 324/307, 309; 382/128; 436/173; 702/19; 128/920
See application file for complete search history.

(56) References Cited

U.S. PATENT DOCUMENTS 6,430,430 B1 *  8/2002  Gosche ................. 600/410

OTHER PUBLICATIONS

Cordato et al. "Frontal atrophy correlates with behavioural changes in progressive supranuclear palsy" 2002, Brain; 125, 789-800.*
Morris et al. "Progressive supranuclear palsy (Steele-Richardson-Olszewski disease)" 1999, Postgrad Med J; 75, 579-584.*
Hutchinson M, Raff U, Parkinson's disease: a novel MRI method for determining structural changes in the substantia nigra. *J Neurol Neurosurg Psychiatry*, Dec. 1999; 67:815-838.
Hutchinson M, Raff U, Structural Changes of the Substantia Nigra in Parkinson's Disease as Revealed by MR Imaging, AJNR *Am J Neuroradiol* 21:697-701, Apr. 2000.

* cited by examiner

*Primary Examiner*—Ruth S Smith
(74) *Attorney, Agent, or Firm*—Cooper & Dunham, LLP (57) ABSTRACT

A method of detecting Parkinson's disease through MRI of substantial nigra pars compacta (SNc) tissue. The method involves obtaining a gray matter suppressed (GMS) MRI signal from the SNc tissue, obtaining a white matter suppressed (WMS) MRI signal of the SNc tissue, and combining information from the GMS and WMS MRI signals to produce resultant signals indicative of Parkinson's disease. A similar method can be used to detect Progressive Supranuclear Palsy. A method of distinguishing between the two diseases involves obtaining at least two starting MRI images of SNc tissue using different MRI parameters, and combining the starting images to compute resultant signals differentiating between the two forms of parkinsonism.

17 Claims, 8 Drawing Sheets

FIG. 1

Ratio images of the substantia nigra pars compacta (SNc) after automated segmentation of the WMS images of the cerebral peduncle.

FIG. 2

**Progressive Supranuclear Palsy
(PSP)**

Upper (WMS / GMS)
Ratio Image

Segmented SNc
(Upper Slice)

Lower (WMS / GMS)
Ratio Image

Segmented SNc
(Lower Slice)

Imaging of the substantia nigra pars compacta (SNc) in Progressive Supranuclear Palsy (PSP). The left column shows the (WMS / GMS) ratio images of upper and lower slices and the right hand side displays the SNc segmented from the WMS images of the cerebral peduncle. Images are displayed using the pseudo color lookup table on the right. Note that the gradient of signal is in the opposite direction to that seen in Parkinson's disease (i.e. there is relative loss of signal medially). This suggests the possibility of distinguishing the two forms of parkinsonism radiographically.

AJNR: 21, April 2000

WMS Image of
Mesencephalon

GMS Image of
Mesencephalon

WMS cerebral Peduncle

GMS cerebral Peduncle

Ratio Image WMS / GMS

Fig. 8

MRI DETECTION AND STAGING OF PARKINSON'S DISEASE AND DETECTION OF PROGRESSIVE SUPRANUCLEAR PALSY

REFERENCE TO RELATED APPLICATION

This present application claims the benefit of provisional Application Ser. No. 60/250,301, filed on Nov. 30, 2000, and hereby incorporates by reference herein the provisional application and its appendices.

FIELD

This patent specification is in the field of magnetic resonance imaging (MRI) and more specifically relates to obtaining and processing MRI signals to identify and stage conditions such as Parkinson's disease.

BACKGROUND

Parkinson's disease is a progressive neurodegenerative condition that is difficult to detect in its early stages. Because of the human and socioeconomic cost of the disease, it is believed that the earliest detection, even when the disease is presymptomatic, is desirable. Further, it is believed that it would be desirable to develop an objective radiologic measure to stage the disease and to assess effect of interventions in both asymptomatic and symptomatic patients.

This patent specification incorporates by reference the following articles: (1) Hutchinson M, Raff U, Parkinson's disease: a novel MRI method for determining structural changes in the substantia nigra. J Neurol Neurosurg Psychiatry December 1999; 67:815-818; and (2) Hutchinson M. Raff U, Structural Changes of the Substantia Nigra in Parkinson's Disease as Revealed by MR Imaging, AJNR Am J Neuroradiol 21:697-701, April 2000.

SUMMARY

In preferred embodiments, two MRI images of different characteristics are obtained for each of a plurality of MRI slices of brain tissue. The images for each slice are combined to enhance a characteristic of interest as compared with the information in either starting image. The combined information is further processed to compute numerical measures indicative of the presence and or staging of a disease.

In one preferred embodiment, the numerical measures are indicative of the presence and/or staging of Parkinson's disease. In another, they are indicative of Progressive Supranuclear Palsy.

The two starting images for an MRI slice can be two images that include the substantia nigra pars compacta (SNc)—a grey matter suppressed (GMS) MRI image and a white matter suppressed (WMS) image. A ratio of the two images produces a ratio image. A ratio of two regions of interest (ROI), one from the medial segment and one from the lateral segment of the SNc for each slice, and combining the measures for two or more slices, gives numerical values indicative of the presence and/or staging of Parkinson's disease and the presence of Progressive Supranuclear Palsy.

The preferred pulse sequences for obtaining the GMS and WMS signals are inversion-recovery sequences. Preferably, the WMS and GMS images, and/or the ratio images, are displayed in pseudocolor for more convenient visual delineation of the SNc. Preferably, an automatic segmentation is used to outline the SNc.

BRIEF DESCRIPTION OF THE DRAWING

FIG. 4 is a copy of Fig. A in article (1) cited above. The Upper row shows upper and lower ratio images of a normal object. Note that the substania nigra pars compacta (SNc) reaches the edge of the peduncle in the upper slice and becomes smaller in the lower slice. The substania nigra pars reticulata (SNR) is also seen in the upper slice, extending into the corticospinal tracts anteriorly. The colour bar shows the psuedocolour used for display and ranges from 0 to 225 (bottom to top). The ratio image of an early case shows, in the upper slice, thinning and loss of signal in the lateral part of the SNc. Note that the lower slice shows islands of destruction. The ratio images of an advanced stage show considerable signal loss in the SNc in both upper and lower slices. In addition, the SNc is essentially reduced to two rings of preservation in the lower slice.

FIG. 6 is a copy of FIG. 1 in article (2) cited above. The upper row displays an example of axial WMS and GMS MR acquisition images of the mesencephalon in a control participant. The cerebral peduncle (second row, left) extracted from the WMS midbrain image serves as a template to extract the GMS image of the cerebral the cerebral peduncle shown on the right. The SNc is seen as bright arch in the peduncular WMS image, whereas it appears as a dark band in the corresponding GMS image. Note also the substantia nigra pars reticula (SNR) reaching across the crus cerebi toward the SNc. The rain image (WMS/GMS) of the two images in the second row yields the color-coded ratio image displayed on the bottom. All black and white images are shown using a standard display of 256 gray levels. The color image uses a 256-pseudocolour lookup table.

DETAILED DESCRIPTION

As described in the two articles cited above and hereby incorporated by reference herein, the possibility of detecting Parkinson's disease using MRI has been a long-sought goal.

In preferred embodiments described herein and in the two articles, this goal is met by using imaging that enhances changes in a brain area that are believed to be indicative of Parkinson's disease. Using a combination of two MRI imaging inversion-recovery sequences, the substantia nigra is imaged and a radiologic index is derived and used to quantify changes in a manner enabling detection even in asymptomatic patients and also enabling objective staging of the disease. Structural changes in the substantia nigra, mainly in the pars compacta (SNc), are highlighted using the preferred MRI signals and processing, and numerical scored are derived to indicate the presence and/or staging of the disease.

In a first method, described in detail in article (1), which is cited above and incorporated by reference herein, a white matter suppressed (WMS) image and a grey matter suppressed (GMS) images are obtained, using MRI inversion-recovery pulse sequences with the parameters stated in article (1) for the indicated MRI scanner, or using other sequences or parameters or MRI scanners that produce WMS and GMS MRI images differing from each other in a manner allowing for processing that highlights changes in the SNc associated with Parkinson's disease. As described in article (1), it has been found that the GMS signal tends to increase in SNc areas affected by the disease while the WMS signal tends to decrease in the same areas. A ratio image of the WMS to GMA MRI images of an MRI slice tends to have an increased sensitivity to changes in the substantia nigra due to Parkinson's disease than either of the GMS and WMS images alone. A numerical measure can be obtained, for example by taking a ratio of a medial-to-lateral regions of interest (ROI) in the substantia nigra imaged in each MRI slice. Each ROI can be about 200 pixels in size, although different sizes can be used, and this can also depend on the pixel resolution of the image. If the substantia nigra is imaged in two slices, an upper slice and a lower slice, a total of four ROI are defined. A ratio RU is computed of the pixel values of the lateral to the medial ROI in the upper slice, and a similar ration RL is computed for the lower slice. The resulting ratio values are further processed as described in article (1) to obtain a pair of numerical measures DU and DL. In a plot of the type illustrated in FIG. 4 of this application, which is the a copy of FIG. A of article (1), the numerical measures DU and DL give points that at in a cluster for Parkinson's disease patients that is well spaced from a cluster for patients without the disease, and also are at different positions for different stages of the disease, thus enabling detection and staging of the disease.

For TR much greater than TE, the ratio image depends only or mainly on T1, so the signal values of the ratio image can be recast in the firm of a T1 map. This is so because for IR pulse sequences the pixel value P(x,y) at a pixel position (x,y) can be expressed as the value of T1 at the same position (x,y), thus creating a T1 map. Such a T1 map can be similarly analyzed to compute similar numerical measures that highlight the presence and staging of Parkinson's disease.

Figure 3:
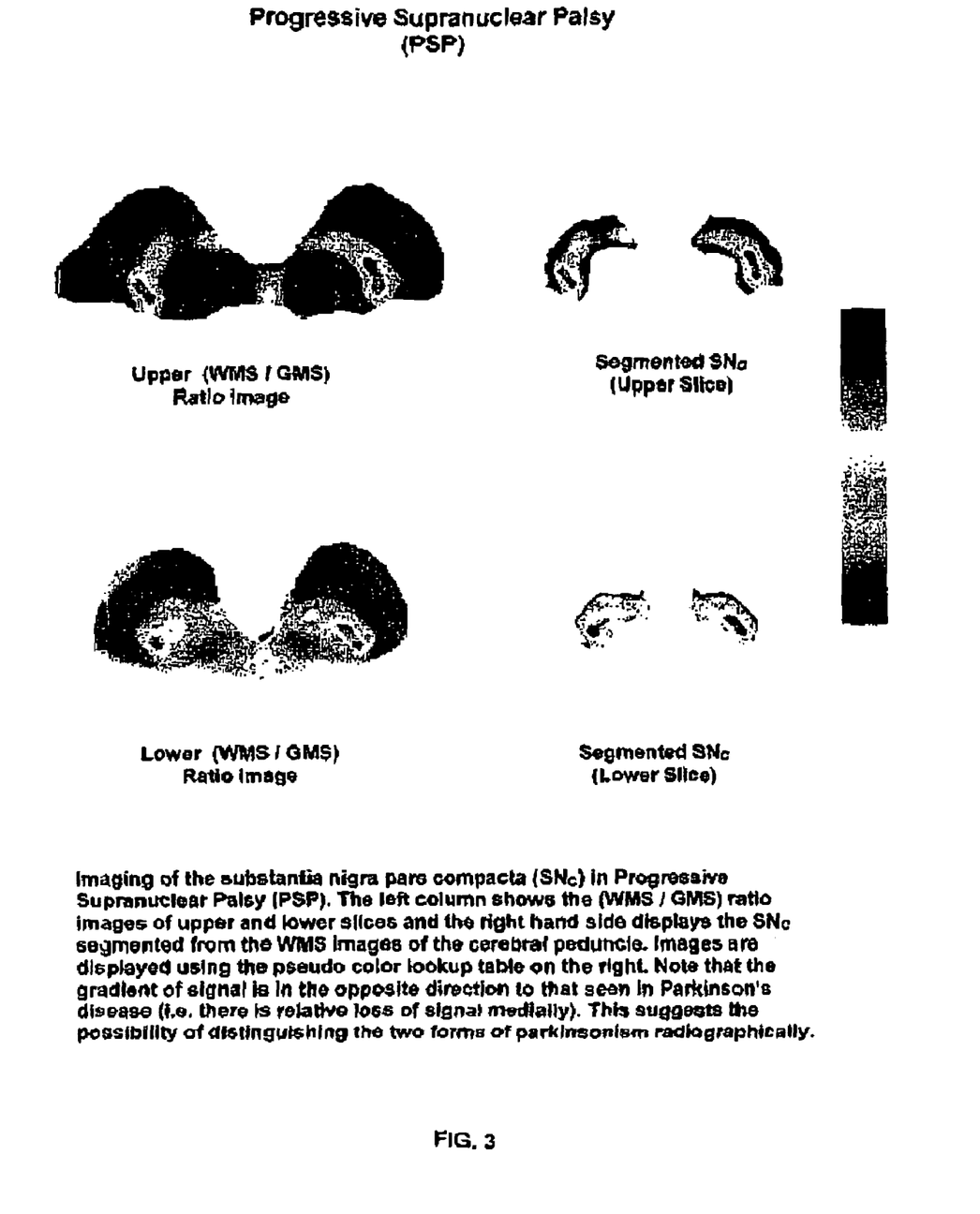
FIG. 3 illustrates imaging of the SNc in Progressive Supranuclear Palsy (PSP).
Figure 4:
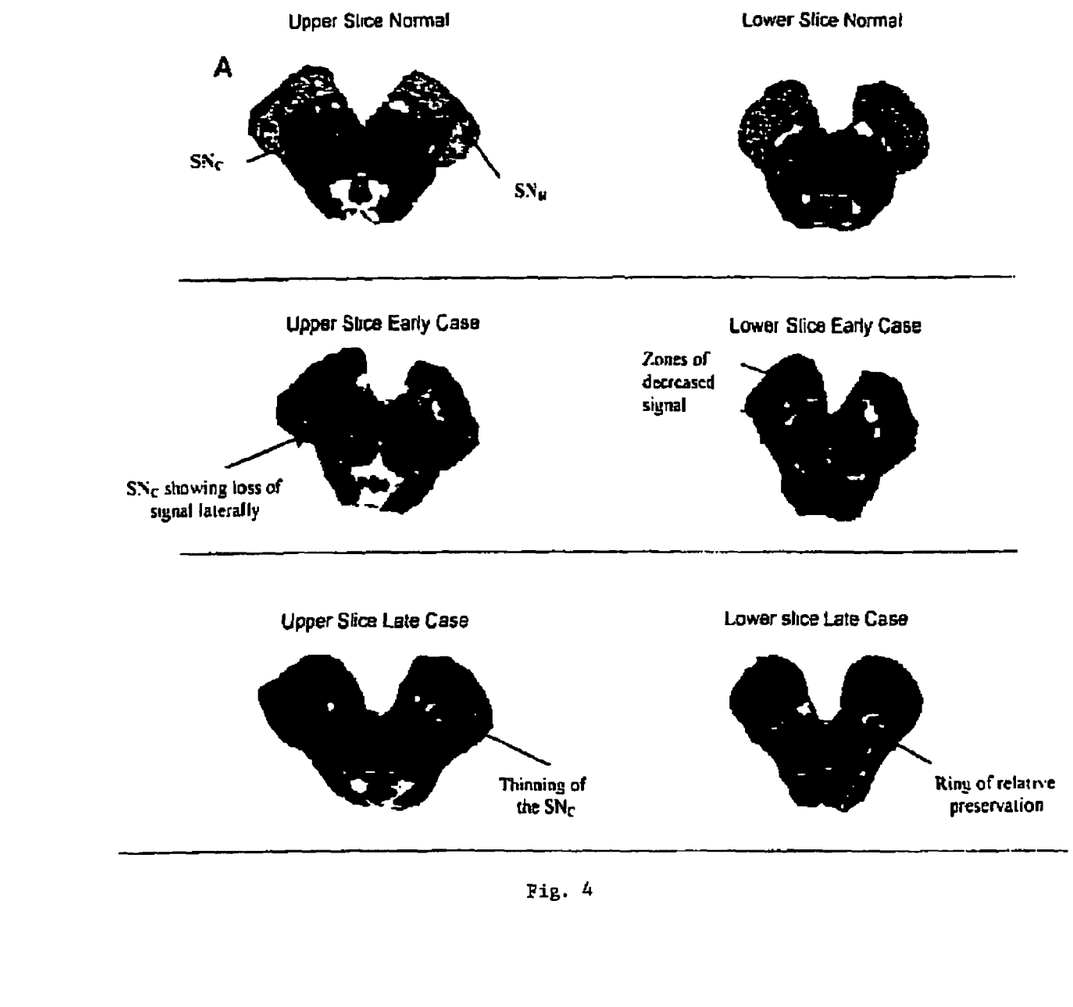

In another embodiment, described in detail in article (2), which is cited above and incorporated by reference herein, WMS and GMA MRI signals are similarly obtained but are processed differently, to compute a numerical radiologic index or score RI that is similarly useful for both detecting and staging Parkinson's disease, as illustrated at FIGS. 3 and 4 of article (2).

Figure 1:
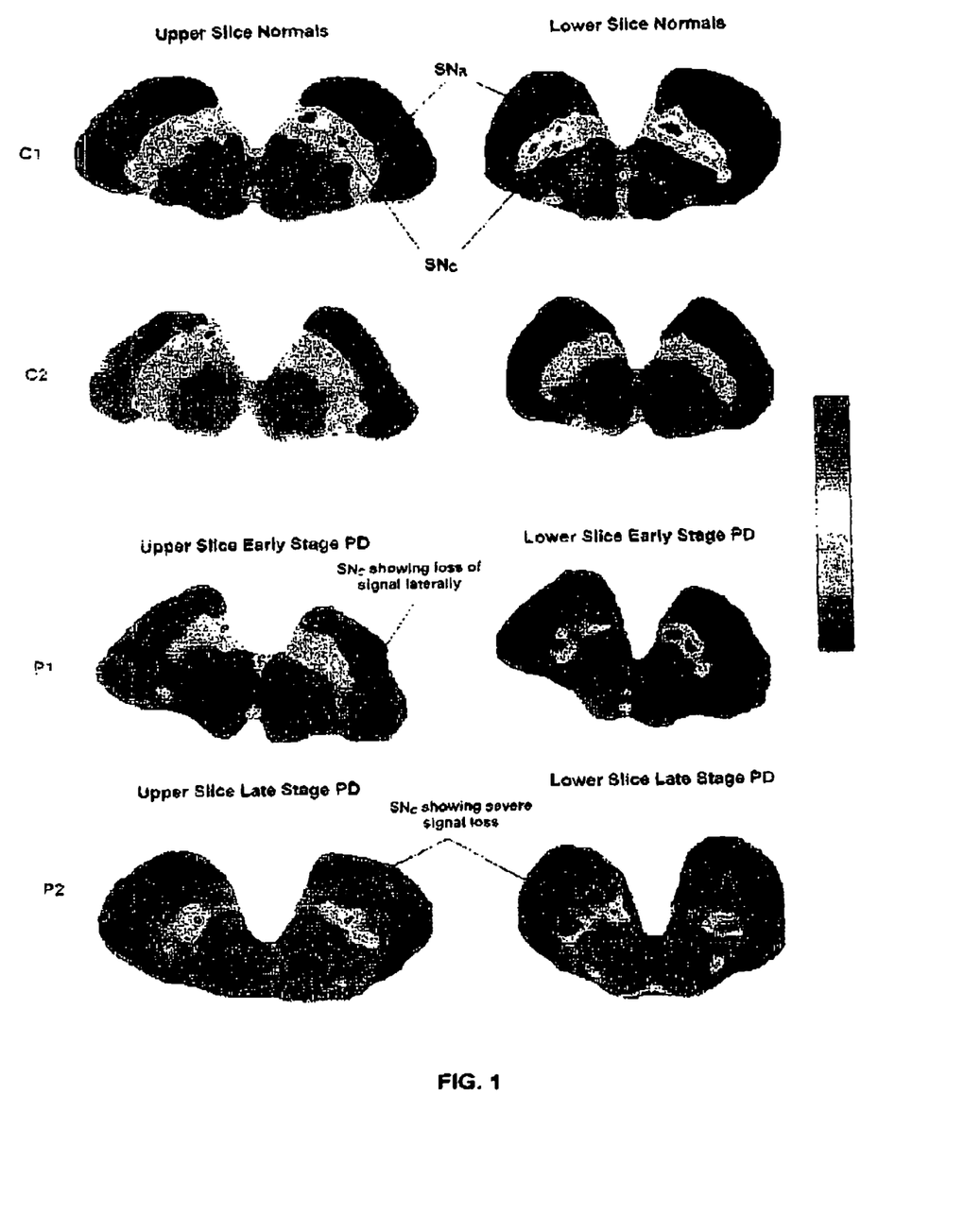
FIG. 1 illustrates grey matter suppressed (GMS) and white matter suppressed (WMS) MRI images that include the substantial nigra pars compacta (SNc) and corresponds to FIG. 2 in article (2) cited above.

FIG. 1 of this patent specification corresponds to FIG. 2 in article (2) and illustrates an example of ratio images of the cerebral peduncle displayed in pseudocolors to show morphologic characteristics of the SNc in two control participants (1 and C2) in a study. The enhanced visualization of changes due to Parkinson's disease can be seen in the lower four images (P1 and P2)

Figure 2:
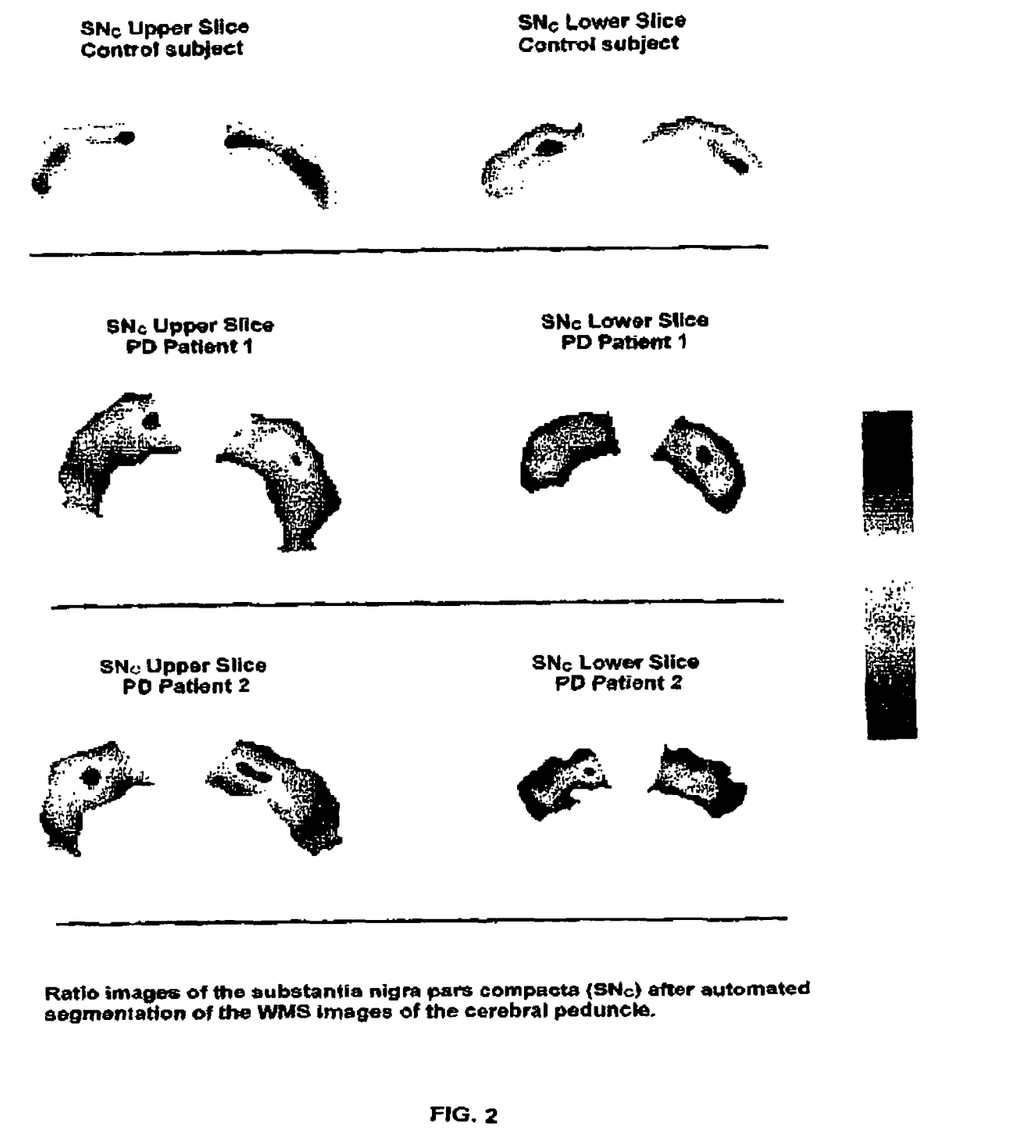
FIG. 2 illustrates ratio images of SNc after automated segmentation of the WMS images of the cerebral peduncle.

FIG. 2 illustrates the results of automated segmentation of the ratio images to isolate the SNc. The segmentation can be carried out with commercially available segmentation software, using pixel values and other parameters that can be experimentally determined for images from a specific MRI scanner.

FIG. 3 illustrates that the WMS and GMS images discussed above and in articles (1) and (2) can be used to provide indications of Progressive Supranuclear Palsy (PSP). As explained in the caption of the figure, the changes that are visualized allow distinguishing between the two forms of parkinsonism radiographically.

FIG. 4 in this patent specification is a non-color copy of Fig. A in article (1) cited above. The Upper row shows upper and lower ratio images of a normal object. The substania nigra pars compacta (SNc) reaches the edge of the peduncle in the upper slice and becomes smaller in the lower slice. The substania nigra pars reticulata (SNR) is also seen in the upper slice, extending into the corticospinal tracts anteriorly. The gray-scale bar shows the shade used for display and ranges from 0 to 225 (bottom to top). The ratio image of an early case shows, in the upper slice, thinning and loss of signal in the lateral part of the SNc. The lower slice shows islands of destruction. The ratio images of an advanced stage show considerable signal loss in the SNc in both upper and lower slices. In addition, the SNc is essentially reduced to two rings of preservation in the lower slice.

Figure 5:
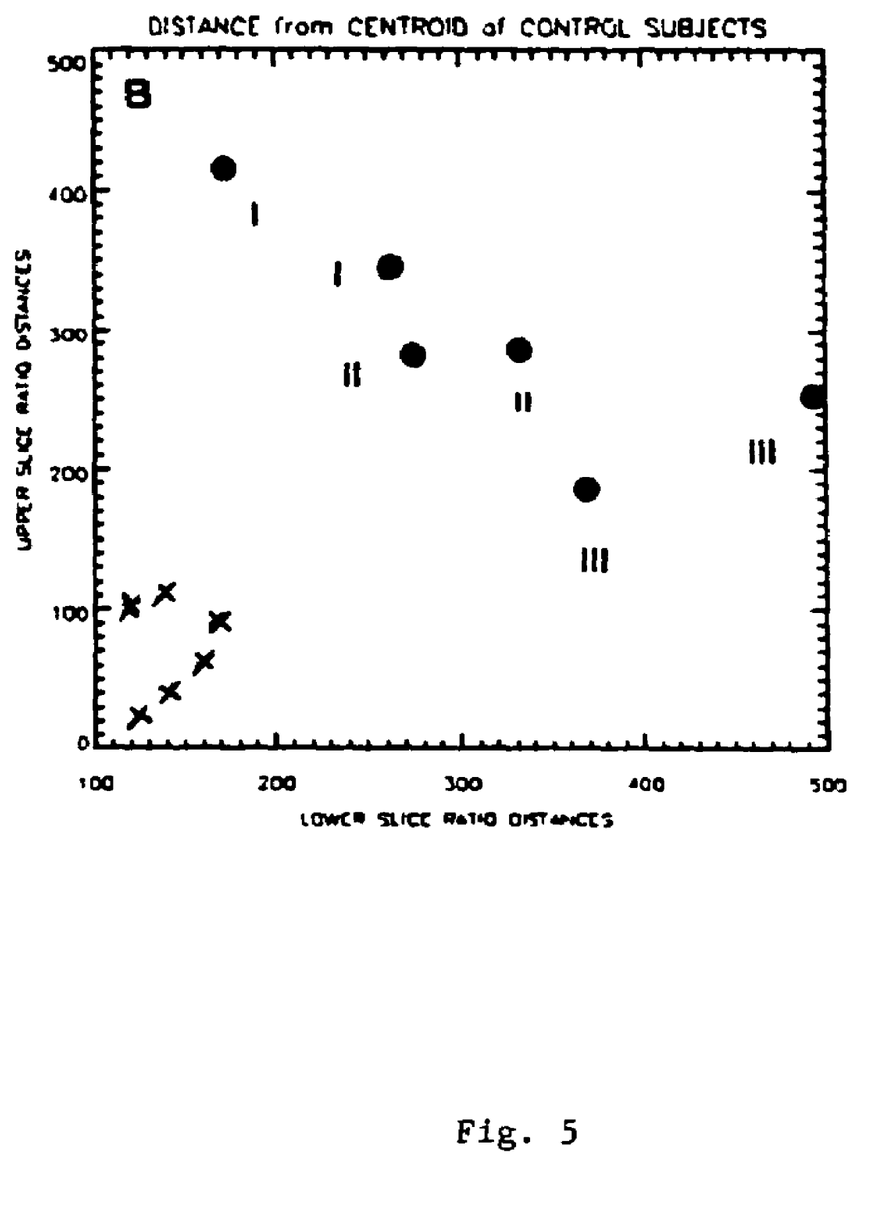
FIG. 5 is a copy of Fig. B in article (1) cited above. The graph is a plot of DU and DL, defined in article (1) as a distance from a centroid of control subjects for the upper slices and lower slices, respectively. Note that the controls (green dots) cluster at the origin and that the patients (red dots) are distributed along a diagonal path in correspondence with Hoehn and Yahr Disease stage (indicated by Roman numeral next to each dot).

FIG. 5 in this patent specification is a non-color copy of Fig. B in article (1) cited above, in which the green dots in the color original are replaced with marks "x". The graph is a plot of DU and DL, defined in article (1) as a distance from a centroid of control subjects for the upper slices and lower slices, respectively. As stated in article (1), left column in page 817, for each subject the ratio R of lateral to medial values was defined, both for the upper slice (RU) and for the lower slice (RL). These values were divided into a ratio for the left SNc, denoted by subscript "1", and the right SNc, denoted by subscript "r". Therefore, each subject in the study was represented by two pairs of values ($RU_1$ and $RU_r$) and ($RL_1$ and $RL_r$), the first pair representing the upper slice and the second the lower. The centroid (the mean value of the ratio) of these values for normal subjects was defined as $\overline{RU}$ and $\overline{RL}$. These values were also defined for both left and right SNc. For each subject (both patients and normal controls) the distance from this centroid was defined as the pair of values (DU, DL), where $$DU = \{(RU_1 - \overline{RU_1})^2 + (RU_r - \overline{RU_r})^2\}^{1/2} \text{ and}$$

$$DL = \{(RL_1 - \overline{RL_1})^2 + (RL_r - \overline{RL_r})^2\}^{1/2}.$$

The controls (marks "x") cluster at the origin and that the patients (dots) are distributed along a diagonal path in correspondence with Hoehn and Yahr Disease stage (indicated by Roman numeral next to each dot).

Figure 6:
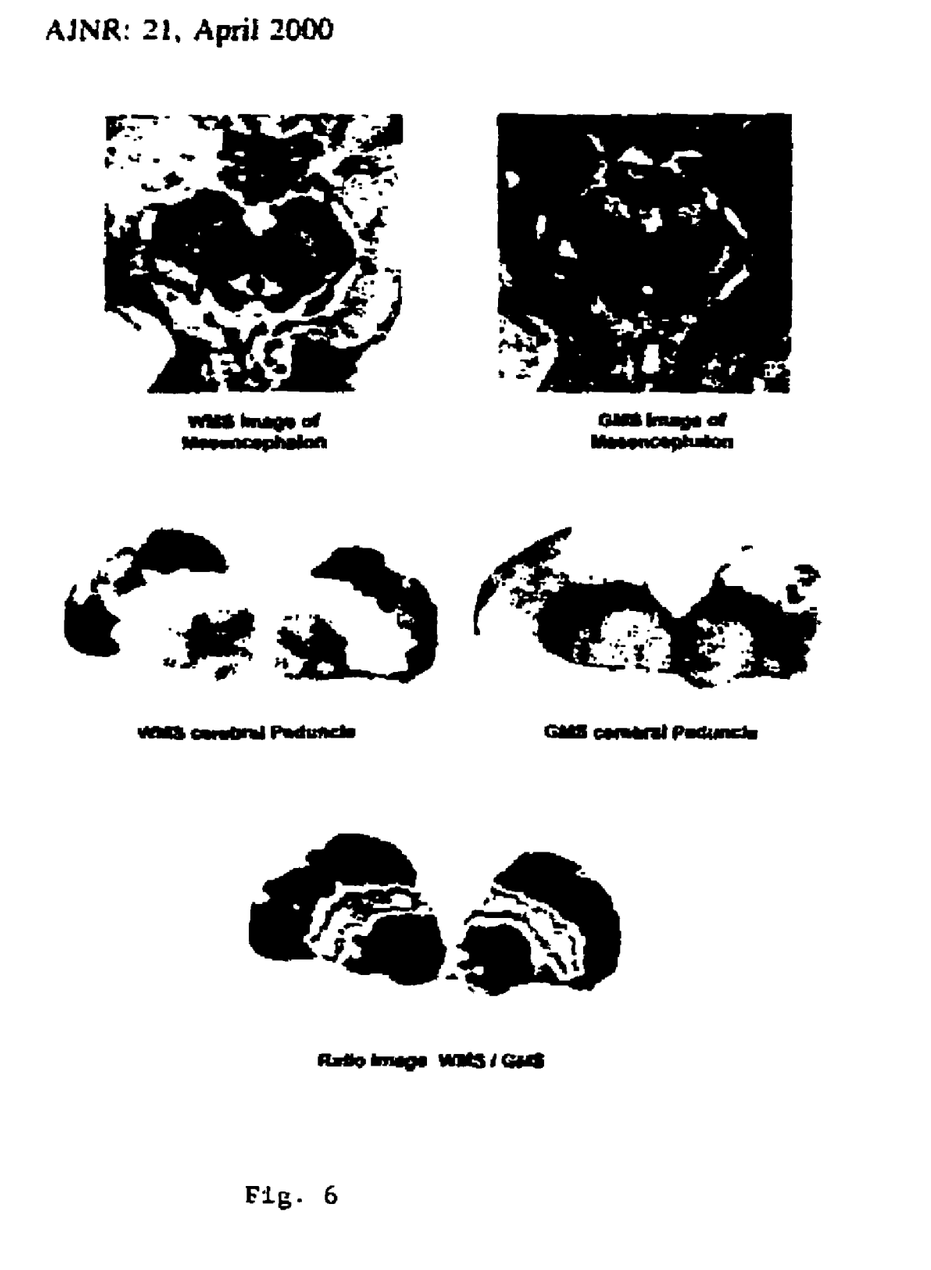

FIG. 6 in this patent specification is a copy of FIG. 1 in article (2) cited above. The upper row displays an example of axial WMS and GMS MR acquisition images of the mesencephalon in a control participant. The cerebral peduncle (second row, left) extracted from the WMS midbrain image serves as a template to extract the GMS image of the cerebral the cerebral peduncle shown on the right. The SNc is seen as bright arch in the peduncular WMS image, whereas it appears as a dark band in the corresponding GMS image. The substantia nigra pars reticula (SNR) reaching across the crus cerebi toward the SNc. The ratio image (WMS/GMS) of the two images in the second row yields the grayscale ratio image displayed on the bottom. All black and white images are shown using a standard display of 256 gray levels. The gray-scale image uses a 256-pseudocolour lookup table.

Figure 7:
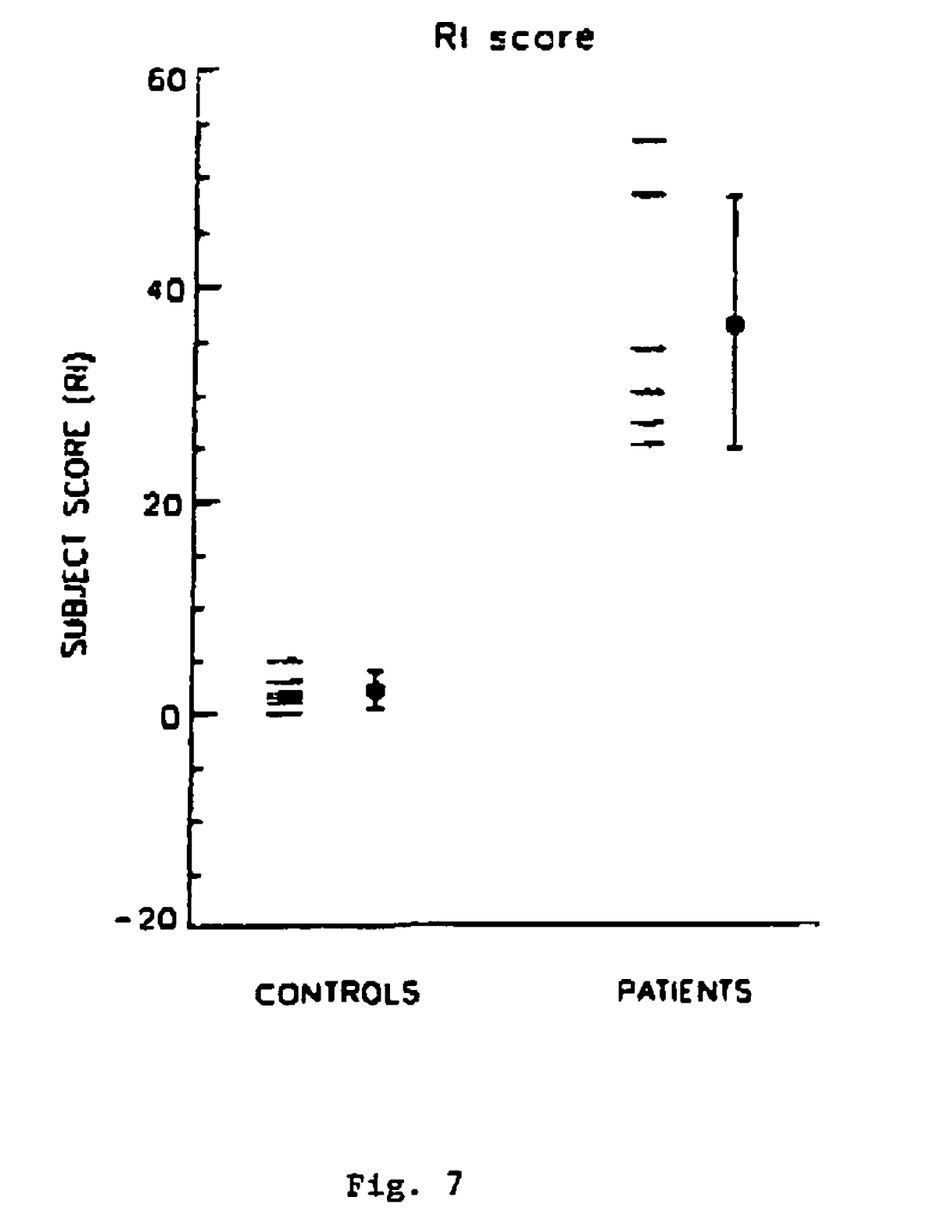
FIG. 7 is a copy of FIG. 3 in article (2) cited above. Radiologic indices are displayed for the six control participants and the six patients with Parkinson's disease. There is no overlap between the groups, which are distinct by Student's t Test (P<0.00005). The error bars represent one SD.

FIG. 7 in this patent specification is a copy of FIG. 3 in article (2) cited above. Radiologic indices are displayed for the six control participants and the six patients with Parkinson's disease. There is no overlap between the groups, which are distinct by Student's t Test (P<0.00005). The error bars represent one SD.

Figure 8:
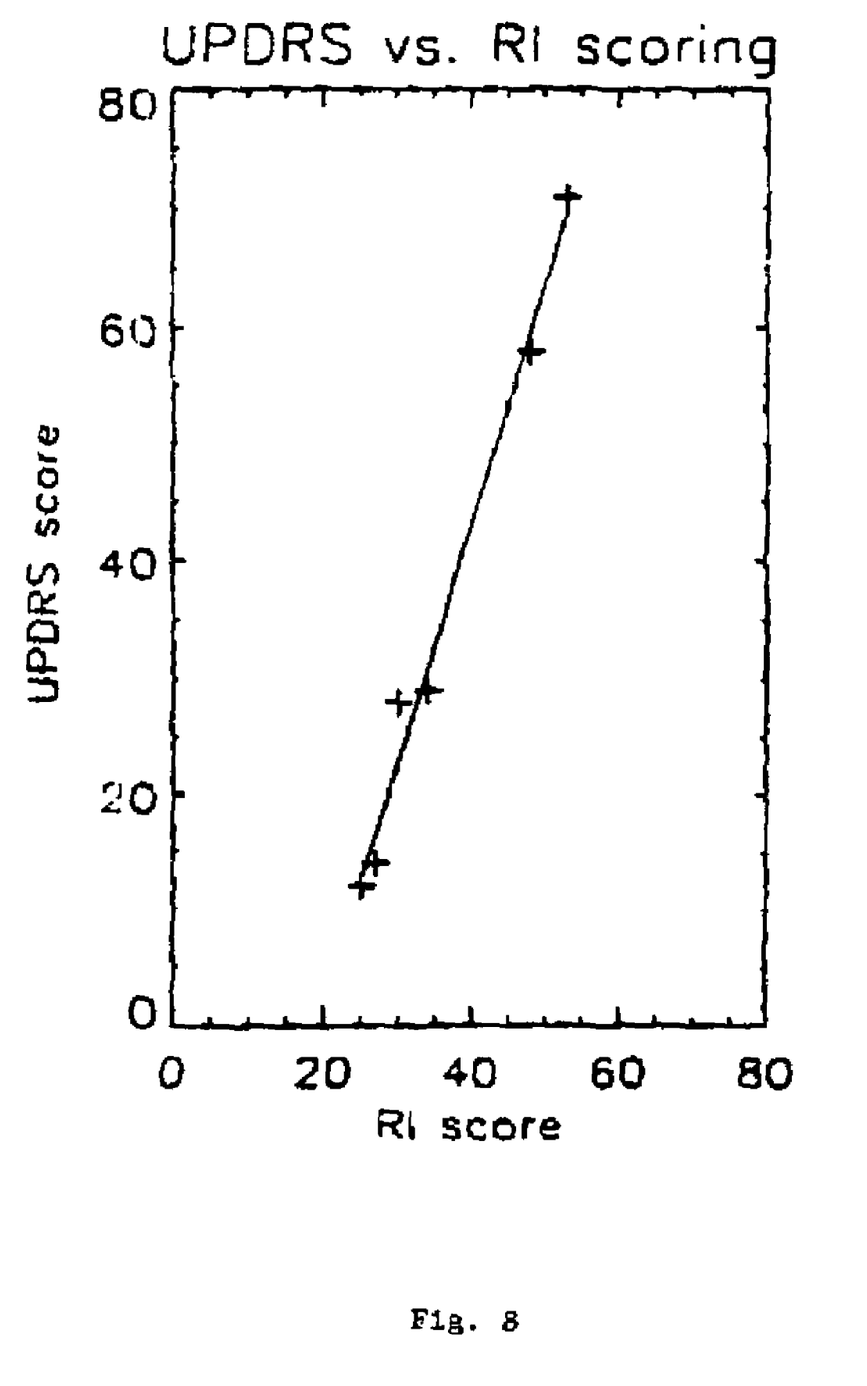
FIG. 8 is a copy of FIG. 4 in article (2) cited above. Unified Parkinson's Disease Rating Scale scores for the six patients ranging from 12 to 71 are plotted versus radio-logic indices. A linear regression analysis was conducted, yielding a linear correlation coefficient of r=0.99.

FIG. 8 in this patent specification is a copy of FIG. 4 in article (2) cited above. Unified Parkinson's Disease Rating Scale scores for the six patients ranging from 12 to 71 are plotted versus radio-logic indices. A linear regression analysis was conducted, yielding a linear correlation coefficient of r=0.99.

While specific examples of embodiments are described in detail above and in the two articles incorporated by reference, it will be clear to those skilled in the relevant technology that alternative implementations are within the scope of the disclosure of the appended claims.

The invention claimed is:

1. A method of detecting Parkinson's disease (PD) through operating a magnetic resonance imaging (MRI) apparatus performing MRI of brain tissue that includes substantia nigra pars compacts (SNc) tissue comprising:
    obtaining a gray matter suppressed (GMS) MRI signal of brain tissue that includes said SNc tissue by operating said MRI apparatus;
    obtaining a white matter suppressed (WMS) MRI signal of brain tissue that includes said SNc tissue by operating said MRI apparatus;
    processing information from said GMS and WMS MRI signals to produce and present resultant signals indicative of PD by computer-processing; and
    including forming and displaying, by computer processing, GMS and WMS images using information from said GMS and WMS signals.

2. A method as in claim 1 in which said obtaining of each of the GMS and WMS MRI signals comprises using an inversion recovery (IR) pulse sequence.

3. A method as in claim 2 wherein said processing of information from said GMS and WMS signals comprises processing at least portions of said GMS and WMS images.

4. A method as in claim 3 in which said processing of information from said GMS and WMS signals comprises obtaining a ratio image of at least portions of said GMS and WMS images for at least one MRI slice.

5. A method as in claim 4 further comprising processing selected medial and lateral regions of interest in each ratio image to derive a numerical measure indicative of the presence and/or staging of PD.

6. A method as in claim 1 further including using the resultant signals to stage PD.

7. A method as in claim 1 including plotting the resultant signals in a two-dimensional plot in which markers for patients with PD appear in an area different from that for patient without PD.

8. A method as in claim 7 in which the markers for patient with PD appear in different areas of the plot corresponding to different stages of PD.

9. A method as in claim 1 including causing said resultant signals to be indicative of a relative loss of MRI signal from lateral as compared with medial portions of the SNc.

10. A method of detecting Progressive Supranuclear Palsy (PSP) through operating a magnetic resonance imaging (MRI) apparatus performing MRI of brain tissue that includes substantia nigra pars compacta (SNc) tissue comprising:
    obtaining a gray matter suppressed (GMS) MRI signal of brain tissue that includes said SNc tissue by operating said MRI apparatus;
    obtaining a white matter suppressed (WMS) MRI signal of brain tissue that includes said SNc tissue by operating said MRI apparatus;
    processing information from said GMS and WMS MRI signals to produce and present resultant signals indicative of PSP by computer-processing; and
    including forming and displaying, by computer processing, GMS and WMS images using information from said GMS and WMS signals.

11. A method as in claim 10 including causing said resultant signals to be indicative of a relative loss of MRI signal from medial as compared with lateral portions of the SNc.

12. A method of distinguishing between two forms of parkinsonism radiographically, Parkinson's disease (PD) and Progressive Supranuclear Palsy (PSP) through operating a magnetic resonance imaging (MRI) apparatus performing MRI of brain tissue that includes substantia nigra pars compacta (SNc) tissue comprising:
    obtaining at least two starting MRI images of brain tissue that includes said SNc tissue using different MRI parameters by operating said MRI apparatus; and
    computer-processing the starting images to compute and present resultant signals differentiating between PD and PSP and displaying results of said computer-processing on display equipment.

13. A method as in claim 12 in which the at least two starting images comprise a gray matter suppressed (GMS) MRI image and a white matter suppressed (WMS) MRI image of brain tissue that includes said SNc tissue in the same MRI slice.

14. A method as in claim 13 in which each of said GMS and WMS image is obtained using an inversion-recovery MRI pulse sequence.

15. A method of detecting Progressive Supranuclear Palsy (PSP) through operating a magnetic resonance imaging (MRI) apparatus performing MRI of brain tissue that includes substantia nigra pars compacta (SNc) tissue comprising:
    obtaining at least two starting MRI images of brain tissue that includes said SNc tissue using different MRI parameters by operating said MRI apparatus; and
    computer-processing the starting images and computing and presenting resultant signals indicative of and identifying PSP and displaying results of said computer-processing on display equipment.

16. A method as in claim 15 in which the at least two starting images comprise a gray matter suppressed (GMS) MRI image and a white matter suppressed (WMS) MRI image of brain tissue that includes said SNc tissue in the same MRI slice.

17. A method as in claim 16 in which each of said GMS and WMS images is obtained using an inversion-recovery MRI pulse sequence.

* * * * *